United States Patent [19]

Doan

[11] Patent Number: 5,087,245
[45] Date of Patent: Feb. 11, 1992

[54] SYSTEM AND METHOD FOR DETECTING ABNORMALITIES IN INTRAVASCULAR INFUSION

[75] Inventor: David Doan, San Diego, Calif.

[73] Assignee: Ivac Corporation, San Diego, Calif.

[21] Appl. No.: 322,291

[22] Filed: Mar. 13, 1989

[51] Int. Cl.[5] .............................................. A61M 31/00
[52] U.S. Cl. .............................. 604/67; 128/DIG. 12
[58] Field of Search ............... 128/DIG. 12, DIG. 13; 604/65–67, 246, 247

[56] References Cited

U.S. PATENT DOCUMENTS

| | | | |
|---|---|---|---|
| 3,853,118 | 12/1974 | Schendel | 128/2 S |
| 4,457,751 | 7/1984 | Rodler | 604/66 |
| 4,460,355 | 7/1984 | Layman | 604/118 |
| 4,534,756 | 8/1985 | Nelson | 604/50 |
| 4,710,163 | 12/1987 | Butterfield | 128/DIG. 13 |
| 4,743,228 | 5/1988 | Butterfield | 604/65 |
| 4,846,792 | 7/1985 | Bobo, Jr. et al. | 604/50 |
| 4,898,476 | 2/1990 | Philip | 604/50 |

FOREIGN PATENT DOCUMENTS 248632 12/1987 European Pat. Off. ............... 604/65

OTHER PUBLICATIONS

Ascer et al., "Components of Outflow Resistance and Their Correlation . . . ", Nov. 84, pp. 817–826.

Primary Examiner—Kyle I. Howell
Assistant Examiner—John P. Lacyk
Attorney, Agent, or Firm—Thomas A. Runk

[57] ABSTRACT

The system and method for detecting abnormalities in infusion of parenteral fluid involves producing perturbation of fluid flow by varying the flow rate of the fluid with respect to an equilibrium flow rate, measuring the pressure level, and measuring the pressure of the fluid over a period of time, to determine equilibrium pressure and a pressure response of the fluid to the perturbation, determining an integral of the difference between the equilibrium pressure and the pressure response, determining resistance to fluid flow, determining a second integral of the difference between the pressure response and equilibrium pressure multiplied by time, and determining compliance by dividing the second integral by the first integral. Resistance and compliance values are displayed, and an alarm is generated when the resistance or compliance parameters fall outside of reference ranges.

47 Claims, 3 Drawing Sheets

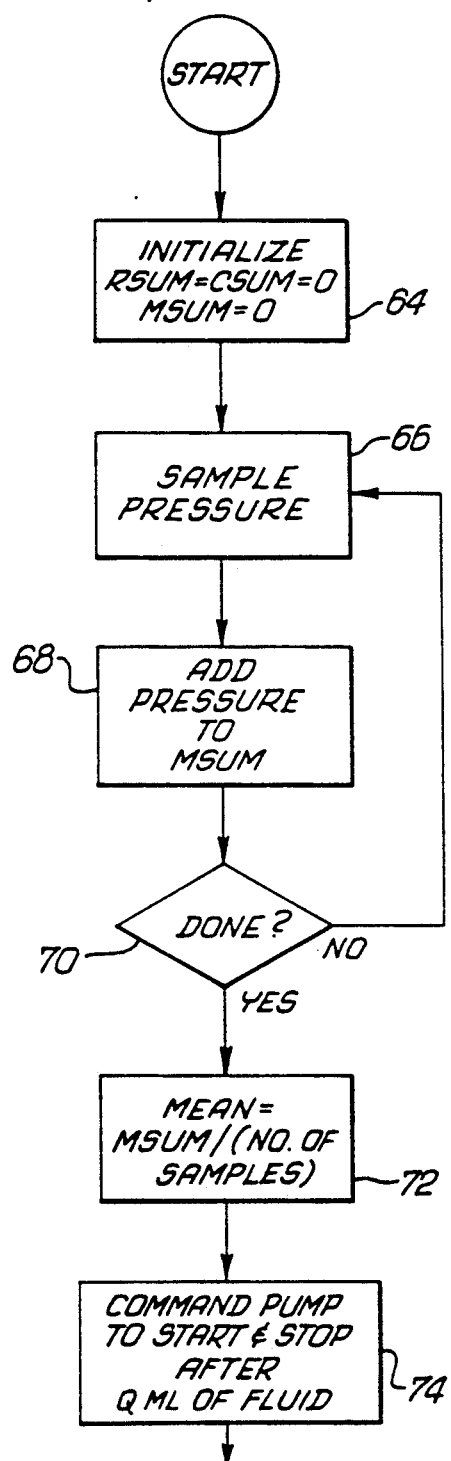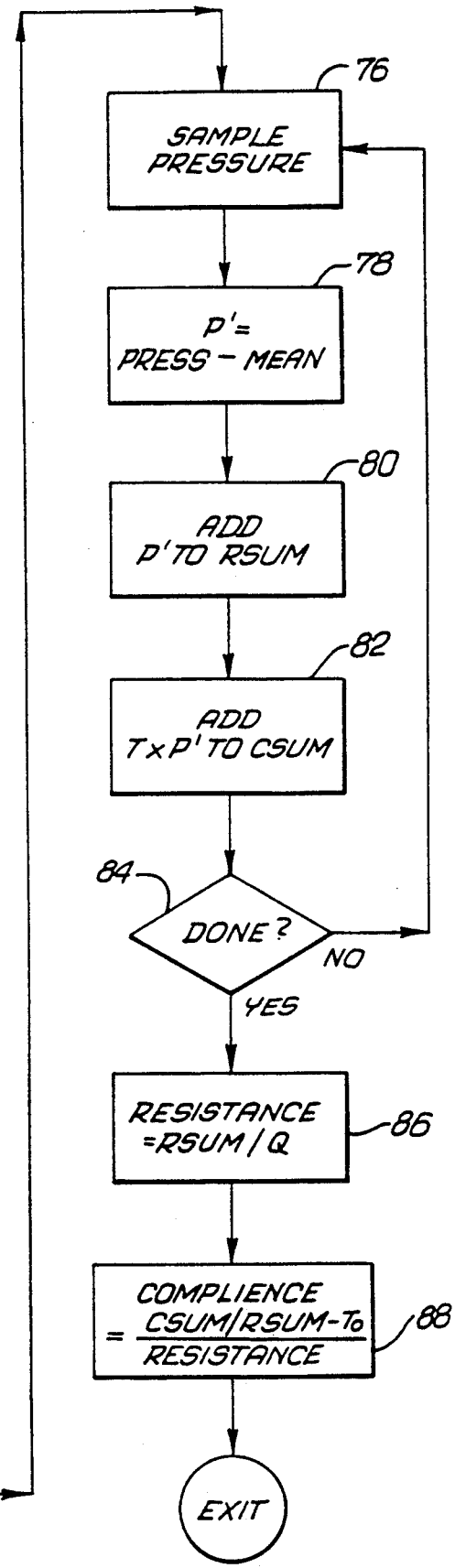
Fig. 3 FLOW CHART OF IRMA/ICARE ALGORITHM

SYSTEM AND METHOD FOR DETECTING ABNORMALITIES IN INTRAVASCULAR INFUSION

BACKGROUND OF THE INVENTION

1. Field of the Invention

This invention generally relates to a system and method for monitoring intravascular infusion of parenteral fluid from a parenteral fluid delivery system to a patient, and more particularly relates to numerical, objective evaluation of effectiveness of intravascular fluid delivery, by monitoring fluid flow parameters of resistance and compliance.

2. Description of Related Art

Systems for infusing parenteral fluids intravenously to a patient by means of an infusion pump typically include a bottle of parenteral fluid, and an intravenous (IV) set which includes a drip chamber, flexible plastic tubing extending from the drip chamber, and a cannula at the end of the tubing to be inserted into a patient's blood vessel for delivery of the parenteral fluid. An infusion pump, such as a peristaltic pump, is typically used for driving the parenteral fluid through the tubing at a desired rate. Common problems in such a system are that the fluid flow may become occluded, that the needle inserted into a patient's vein may be dislodged, or that the discharge tip of the needle becomes partially dislocated so as to deliver fluid in adjacent interstitial tissue, which may cause serious injury.

Systems have been devised for the detection of abnormalities in an intravascular infusion system, by use of simple monitoring of the infusion pressure. A high or increasing pressure may be interpreted as either an infiltration or an occlusion. A low pressure may be interpreted as as an unobstructed line. However, the pressure required to achieve a given flow in an intravascular system depends on many factors, such as motion and position of the patient, respiration and arterial or venous blood pressure of the patient, and the size and position of the cannula used. Such factors create a considerable uncertainty in the measurement of pressure, and may cause difficulty in interpretation of pressure readings. Observation of a pressure response of the fluid delivery system, to determine whether pressure returns to a normal steady state equilibrium within a given time period can give some information as to effectiveness of fluid delivery. Application of fluid flow excitation pulses and comparison of pressure responses of the system against a reference value is also known.

It would be desirable to provide a system for monitoring fluid in an intravascular parenteral fluid delivery system which provides a measure of resistance to fluid flow and a measure of compliance of the patient's tissue. Resistance to flow is appropriate for monitoring flow to an infusion site, since it can indicate such problems as having the end of the cannula pressed against the vein or artery wall, the cannula being infiltrated into the tissues surrounding the vessel, and certain medical problems such as phlebitis which involve constriction of the vessel. Compliance may be used for distinguishing the location of the cannula due to a significant difference between the compliance of a vein and the compliance in interstitial tissue.

SUMMARY OF THE INVENTION

The present invention provides a system and method for detecting abnormalities in infusion of parenteral fluid in a parenteral fluid delivery system having a normal equilibrium flow rate, to provide an indication of the resistance and compliance of the entire fluid flow system, including the patient venous system, by comparing at least one of the indications of the system with a corresponding reference value.

Briefly, and in general terms, the system for detecting abnormalities in infusion of parenteral fluid delivery system to a patient comprises an infusion means for producing a perturbation of the fluid flow by varying the flow rate of the fluid with a predetermined volume of fluid; a sensor for measuring fluid pressure to give an indication of the pressure response; a first integrator means responsive to the pressure measurement for determining the integral of the difference between equilibrium pressure and the pressure response over time; means to give an indication of resistance to fluid flow based upon the first integral; a second integrator means also responsive to the pressure response and equilibrium pressure over time to provide an integral of the product of time and the difference between the pressure response and the equilibrium pressure over time; and means for determining compliance from this second integral by dividing the second integral by the first integral.

The method of the invention, briefly and generally, also concerns the detection of abnormalities in infusion of parenteral fluid from a parenteral fluid delivery system to a patient with the steps comprising producing perturbation of fluid flow by varying the flow rate of the fluid from the equilibrium flow rate with a predetermined volume of fluid; measuring the pressure of the fluid over time; determining a first integral of the difference between the equilibrium pressure and the pressure response over time; determining resistance to fluid flow based upon the first integral; determining a second integral by multiplying the difference between the pressure response and the equilibrium pressure by time, and integrating the result with respect to time; and determining an indication of compliance of the fluid delivery system by dividing the second integral by the first integral.

The principles on which the invention is based are basically as follows:

If a known quantity of fluid is injected into a patient through into a fluid delivery system which is essentially in equilibrium (though not necessarily at zero flow), it will, in general, cause a rise in the pressure. The pressure rise may be sudden or slow, and may even be oscillatory if the hydraulic system is of second or higher order and is underdamped. If the injection of fluid is now stopped, and if the system has an outlet, fluid will leave the system until it is again in equilibrium with its surroundings. Unless the hydraulic system is permanently deformed by the fluid injected into it, the amount of fluid leaving will be equal to the amount of fluid which entered.

If the outflow of fluid as a function of time (t), due to the difference in pressure between the system and its surroundings, is designated "F(t)", the background or equilibrium flow is designated by "$F_{eq}$", the pressure as a function of time (t) within the system is designated by "P(t)", and the equilibrium pressure is designated by "$P_{eq}$", then the resistance to flow may be defined by $$R = \frac{P(t) - P_{eq}}{F(t) - F_{eq}} \qquad \text{Eq. 1}$$

The time-varying pressure, P(t), is readily measured. The time-varying flow, F(t) is not.

Rearranging Eq. (1):

$$R(F(t) - F_{eq}) = P(t) - P_{eq}.\qquad\text{Eq. 2}$$

integrate both sides over time. Since R is a constant, $$R\int_{-\infty}^{\infty}(F(t) - F_{eq})dt = \int_{-\infty}^{\infty}(P(t) - P_{eq})dt,\qquad\text{Eq. 3}$$

or $$R = \frac{\int_{-\infty}^{\infty}(P(t) - P_{eq})dt}{\int_{-\infty}^{\infty}(F(t) - F_{eq})dt}\qquad\text{Eq. 4}$$

But the denominator is just $$\int_{-\infty}^{\infty}(F(t) - F_{eq})dt = Q\qquad\text{Eq. 5}$$

which is the known quantity of fluid injected into the system. Thus, $$R = \frac{\int_{-\infty}^{\infty}(P(t) - P_{eq})dt}{Q},\qquad\text{Eq. 6}$$

The measurement of compliance may be understood by considering a parallel resistance-compliance model. The pressure is given by $$P(t) - P_{eq} = \frac{1}{C}\int_{0}^{t}\left((F(t') - F_{eq}) - \frac{P(t') - P_{eq}}{R}\right)dt.\qquad\text{Eq. 7}$$

Integrating both sides with respect to t gives $$\int_{0}^{T}(P(t) - P_{eq})dt = \frac{1}{C}\int_{0}^{T}\int_{0}^{t}(F(t') - F_{eq})dt'\,dt -\qquad\text{Eq. 8}$$
$$\frac{1}{RC}\int_{0}^{T}\int_{0}^{t}(P(t') - P_{eq})dt'\,dt$$

Integrating the double integrals by parts gives $$\int_{0}^{T}(P(t) - P_{eq})dt =\qquad\text{Eq. 9}$$
$$\frac{1}{C}\left[T\int_{0}^{T}(F(t) - F_{eq})dt - \int_{0}^{T}t(F(t) - F_{eq})dt\right] -$$
$$\frac{1}{RC}\left[T\int_{0}^{T}(P(t) - P_{eq})dt - \int_{0}^{T}t(P(t) - P_{eq})dt\right]$$

By using Equation 3 and letting T approach infinity, where $T_{\mathit{eff}}$ is the effective time of response, the final result is $$T_{\mathit{eff}} = RC = \frac{\int_{0}^{\infty}t(P(t) - P_{eq})dt}{\int_{0}^{\infty}(P(t) - P_{eq})dt} - \frac{\int_{0}^{\infty}t(F(t) - F_{eq})dt}{\int_{0}^{\infty}(F(t) - F_{eq})dt}.\qquad\text{Eq. 10}$$

This derivation is not rigorous; it is possible to show, however, that if the system is in equilibrium with its surroundings before the fluid is injected into it, and the integral is done over sufficient time for the system to again return to equilibrium, then Eq. 6 gives the total resistance to flow from the point of the pressure measurement to the ambient pressure sink into which the system drains. The value of resistance so obtained is unaffected by any combination of compliances and inertances. Their only effect is to determine the time required for the system to return to equilibrium.

Similarly, Eq. 10 gives the effective time constant ($T_{\mathit{eff}}$) of the system. An effective compliance may be obtained by dividing the effective time constant by the total resistance obtained from Eq. 6.

The integrals, $$\frac{\int_{0}^{\infty}t(F(t) - F_{eq})dt}{\int_{0}^{\infty}(F(t) - F_{eq})dt}\qquad(11)$$

which appear in the equations above is to be evaluated from the known timing and flow characteristics of the infusion pump or other flow control device.

The methods described do not require that the "equilibrium state" be a state of zero flow. The equilibrium is rather a dynamic one, which is monitored and determined periodically. It is only necessary for the hydraulic system to be in equilibrium prior to the injection of the bolus, and the pressure response be integrated until it again returns to equilibrium. The baseline pressure, $P_{eq}$, is then the average pressure (including that due to flow) in the equilibrium state, and Q is the difference between the fluid volume delivered and that volume which would have been delivered had there been no bolus injected to perturb the system. In this case, it should be noted that the "bolus" may be negative. That is, the measurement of resistance may be made by using a decrease or an interruption of flow. In this case, Q will be negative. Other patterns of flow perturbation, such as alternatively increasing and decreasing the flow rate, may also be used and have the potential advantage of providing a greater immunity to error caused by pressure changes due to other causes.

It is not even necessary that the "equilibrium state" be a steady state. It has been shown experimentally that if the integrals in Eqs. 6, 10, and 11 are evaluated synchronously with the repetitive or cyclic action of a peristaltic pump, then the values so obtained are stable with time, and accurately report the resistance and compliance.

It is also important to note that the method puts no limit on the size, duration, or rise time of the injected bolus. It is sufficient to start with the system in equilibrium, perturb the flow, and integrate the difference between the resulting pressure response and the equilibrium pressure until equilibrium is again achieved. The integration provides a natural filter which minimizes the effects of vibration of the infusion set tubing, and patient motion. Since the length of the flow perturbation is not related to the time required for equilibrium to return, it can be made quite short, which provides a major advantage at low flow rates. A short pulse of fluid can be used, which, since it represents a high instantaneous rate, will produce an easily measurable pressure response. The volume can still be quite small, on the order of a few microliters. At higher rates, rather than waiting for equilibrium to return, integration taken over the period of perturbation reduces the length of time required for a resistance measurement. Clinically, this means that in the case of an infiltration, less fluid is delivered into the tissue before the condition is indicated.

Other aspects and advantages of the invention will become apparent from the following detailed description, and the accompanying drawings, illustrating by way of example the features of the invention.

BRIEF DESCRIPTION OF THE DRAWINGS

FIG. 3 illustrates a flow chart of the controlling algorithm performed by the system;

DETAILED DESCRIPTION OF THE INVENTION

Figure 1:
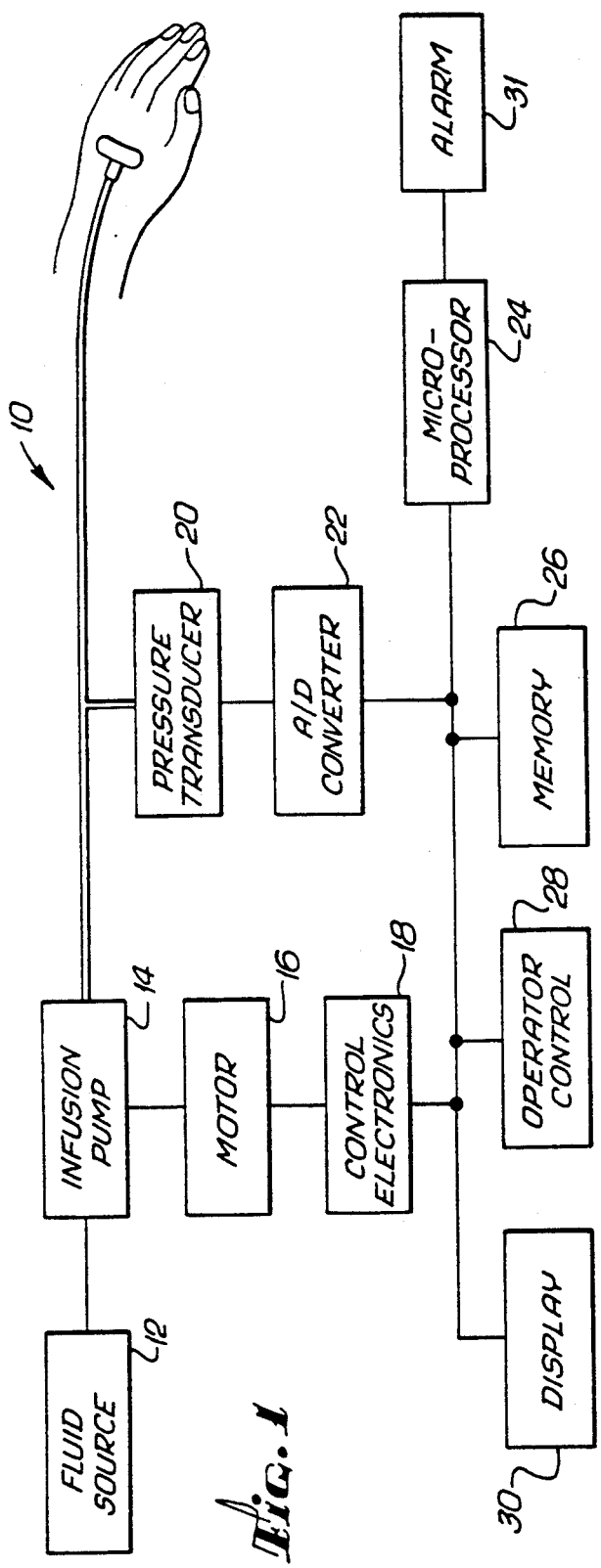
FIG. 1 is a simplified block diagram of a system for detecting abnormalities in intravascular infusion of parenteral fluid from a parenteral fluid delivery system to a patient.

As is shown in the drawings for purposes of illustration, the invention is embodied in a system and method for detecting abnormalities in infusion of parenteral fluid from a parenteral fluid delivery system to a patient which normally operates at an equilibrium pressure level. The parenteral fluid delivery system is herein defined as including not only the tubing of the fluid administration system, but also the venous system and tissue of the patient, since the venous and tissue response of the patient affect the effectiveness of the fluid administration as well, and are, practically speaking, of primary interest. The detection system provides an indication of the resistance and compliance based upon the monitoring of fluid pressure. The detection system is particularly suited for use at low flow rates, although it is not limited to low flow rates.

In accordance with the invention, there is provided a system for detecting abnormalities in infusion of parenteral fluid from a parenteral fluid delivery system to a patient, the system having an equilibrium flow rate, and comprising infusion means for producing a perturbation of the fluid flow by varying the rate of fluid flow from the equilibrium flow rate with a specific volume of fluid; sensor means for measuring pressure of the fluid over a period of time adapted to generate a signal representing a pressure response of the fluid to the perturbation and a signal representing an equilibrium pressure level; first integrator means for determining a first integral of the difference between the equilibrium pressure signal and the pressure response signal over time, and adapted to generate a signal representing the first integral; means for determining resistance to fluid flow in the delivery system adapted to scale the first integral signal according to the specific volume to produce a signal representing resistance to fluid flow; second integrator means for determining a second integral by multiplying the difference between the pressure response signal over time and the equilibrium pressure signal by a value representing the time, and integrating the resultant product with respect to the time, and adapted to generate a signal representing the second integral; and means for determining compliance of the fluid delivery system by dividing the second integral signal by the first integral signal and scaling the resultant quotient according to the previously determined resistance to produce a signal representing compliance of the fluid delivery system.

The invention also provides for a method of detecting abnormalities in infusion of parenteral fluid from a parenteral fluid delivery system to a patient, the system having an equilibrium flow rate, comprising the steps of producing a perturbation of the fluid flow by varying the rate of fluid flow from the equilibrium flow rate with a specific volume of fluid; measuring the pressure of the fluid over a period of time, generating a signal representing an equilibrium pressure level, and generating a signal representing a pressure response of the fluid to the perturbation; determining a first integral of the difference between the equilibrium pressure signal and the pressure response signal over time, and generating a signal representing the first integral; determining resistance to fluid flow in the delivery system by scaling the first integral signal according to the specific volume, and generating a signal representing resistance to fluid flow; determining a second integral by multiplying the difference between the pressure response signal over time and the equilibrium pressure signal by a value representing the time, and integrating the resultant product with respect to the time, and generating a signal representing the second integral; determining compliance of the fluid delivery system by dividing the second integral signal by the first integral signal to produce a signal representing an effective time constant of the fluid delivery system, and scaling the time constant signal by the previously determined resistance to produce a signal representing compliance of the fluid delivery system.

As is shown in the drawings, a parenteral fluid delivery device 10 includes a fluid source 12, connected to an infusion pump 14, which is preferably a peristaltic pump, driven by a motor 16, and having control electronics 18 for governing the infusion pump for producing perturbations of the fluid flow by varying the rate of fluid flow with respect to the equilibrium flow rate. The infusion pump provides a specific volume of fluid in producing the perturbation, although the volume and pressure may actually be a negative value. For example, the fluid flow rate may be increased above the original flow rate, then allowed to return to the original flow rate, and decreased to a rate below the original fluid flow rate, before finally returning the flow rate to the original rate. The volume may be predetermined or may be dynamically determined, to suit the requirements for meaningful measurements. The control electronics may include a variable duty cyclic controller, to allow production of cyclic perturbation, which can be varied either in a predetermined manner, or may also be dynamically according to requirements for meaningful measurements. The infusion pump is preferably adapted to produce either long or short pulses of flow, which may also be produced in a cyclic pattern, determined in advance. A pressure transducer 20 in line with the fluid flow to the patient, generates an analog pressure signal which is converted to a digital signal by A/D converter 22, to provide the system with measurements of pressure before, during and after the perturbation of fluid flow. Although the determination of equilibrium pressure may be based upon a measurement of pressure in the system before the perturbation of fluid flow alone, equilibrium pressure is preferably averaged over a number of pressure readings both before and after the measurement of the pressure response to the perturbation of flow. Further noise reduction techniques, such as exclusion of high and low values, can also be used. Such averaging and noise reduction techniques are also preferably used in determining effective resistance, compliance, and time constant values.

The means for calculating the first integral and the second integral is preferably a microprocessor 24. While use of a microprocessor is preferred, it would also be possible to utilize electrical analog means for generating signals representing the first and second integrals. Associated with the microprocessor is a memory 26, for receiving and storing the values generated in calculating the equilibrium pressure level, the first integral, the second integral, the resistance, and the compliance, and associated predetermined reference values and alarm criteria. Operation of the detection system is provided for by the operator control 28. Further associated with the microprocessor, memory, and operator control is the display unit 30, for displaying any one or more of the parameters determined by the microprocessor. Further associated with the microprocessor is an alarm 31, responsive to comparison of system parameters in comparison to reference values which are stored in the system memory either individually or as a total pattern. Reference values may be input into the memory at the operator control, or may be preprogrammed using signals or values representing ideal parameters which have been calculated from a mathematical model of a fluid delivery system.

Figure 2:
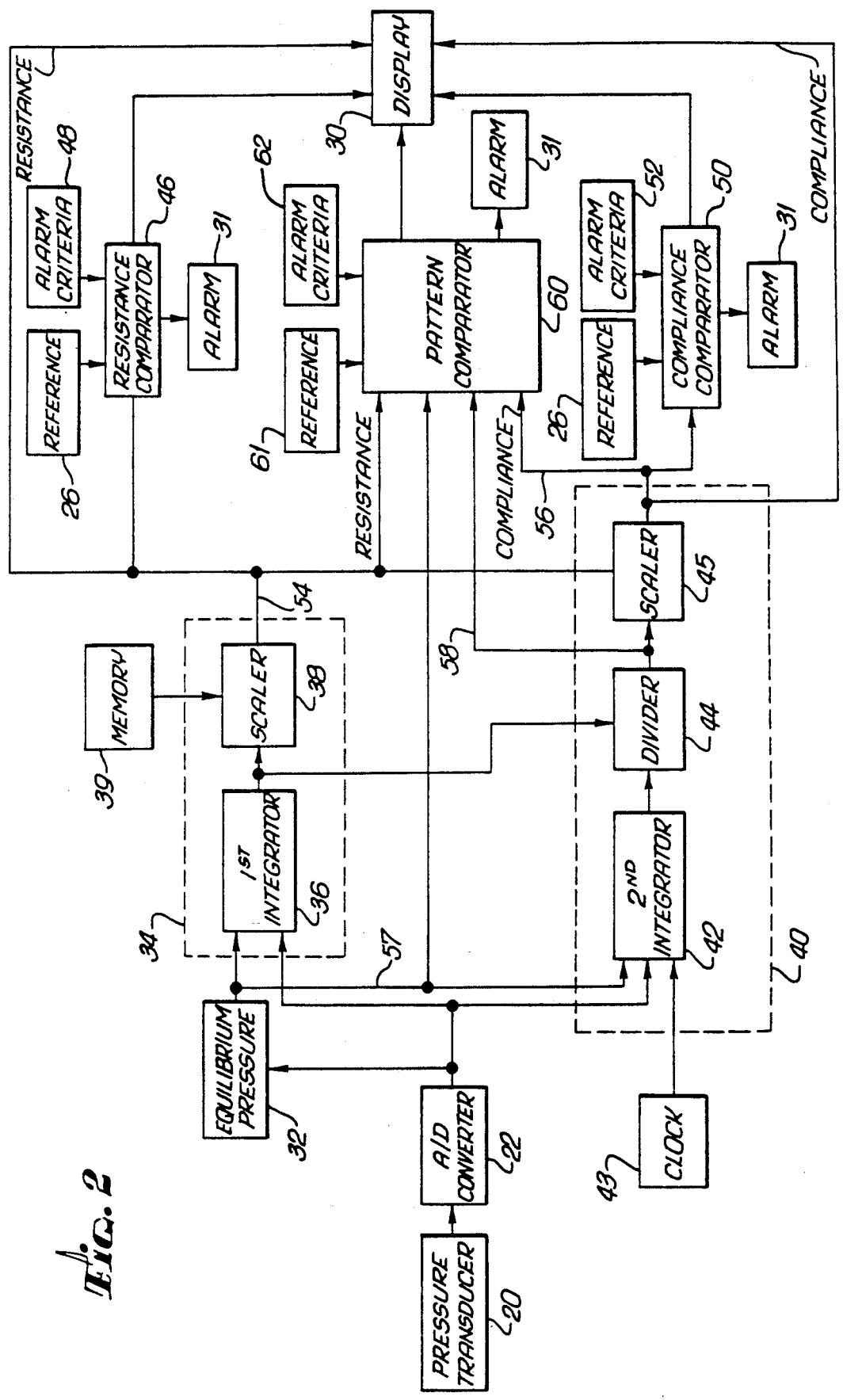
FIG. 2 is a schematic diagram illustrating a system for determining and operating upon the fluid flow parameters of resistance and compliance.

A more detailed illustration of the circuitry utilized in the invention for determination of the system parameters of resistance and compliance is illustrated in FIG. 2. An equilibrium pressure calculator 32 generates a signal representing the equilibrium pressure level of the fluid in the fluid delivery system from measurements of pressure at times when the fluid flow is not perturbed. The resistance calculator 34 includes the first integrator 36 for calculating the difference between the equilibrium pressure signal and a pressure response signal over time, and is adapted to generate a signal representing the first integral. The first integral signal is scaled in the scaler section 38 according to the volume (Q) of the perturbation, which may be either preprogrammed in the system memory 39 or set manually by the operator control. Dividing the first integral by the volume of perturbation provides an indication of the resistance to fluid flow, which may then be represented in the display 30.

The compliance calculator 40 generally includes the second integrator calculator 42 for multiplying the difference between the pressure response signal over time and the equilibrium pressure signal by measured time of perturbation provided by the clock 43, and for integrating the resultant product with respect to the period of time, to generate a signal representing the second integral. The signal representing the second integral is divided by the signal representing the first integral at divider 44, and the resultant quotient is then scaled in scaler section 45 according to the previously determined resistance to produce a signal representing compliance. The compliance signal may be routed to be displayed at 30, for monitoring along with the other indications of fluid flow.

A resistance comparator 46 compares the resistance signal with a reference value from the memory. If the comparison determines that there is a significant difference according to an alarm criteria provided at 48, a signal is generated to activate the alarm 31. Similarly, the compliance signal generated is compared in a compliance comparator 50 with reference values from the memory, and the amount of deviation may be displayed at 30. If the comparison results in a significant difference between the compliance and the reference value, according to an alarm criteria 52 for the compliance, an alarm signal is generated.

The system also preferably provides for a set of parameters for monitoring the operation of the system as a whole. The system further provides a pattern comparator 60 for receiving the resistance signal 54, the effective compliance signal 56, the equilibrium pressure signal 57, and the effective time constant signal 58, to compare these signals taken together with a pattern for corresponding reference signals for determining a total pattern of deviation. The pattern comparator compares the total pattern of deviation with alarm criteria 62, to generate a signal representing the deviation for display at 30, or to generate an alarm signal to the alarm when the total deviation pattern falls outside a predetermined range of values.

With reference to FIG. 3, the operational steps in detecting abnormalities in the intravascular infusion of parenteral fluid to a patient will be described. The flow chart of FIG. 3 illustrates the basic principles of the method, and is representative of the manner in which the algorithms described above are implemented at low flow rates, where the pump is operated for a short period of time and then stopped. This yields a short pulse or perturbation of the fluid flow. For the sake of simplicity, the equilibrium pressure is illustrated as being determined prior to the perturbation in the flow rate. However, it is preferable to use as the equilibrium pressure the average of the equilibrium pressure determined before the perturbation and the equilibrium pressure determined after the perturbation period. This provides considerable immunity from artifacts such as pressure changes due to patient motion. In addition, it should be noted that the loops in the flow chart which implement the repeated sampling of the pressure signal are intended to be timed, so the samples are equally spaced in time. A typical time is 0.005 seconds.

A preferred mode of carrying out the method of the invention involves control of the steps of the method by a microprocessor or microcomputer. The integrals RSUM and CSUM utilized for determining resistance and compliance, and the equilibrium pressure value MSUM, are initialized at 64. Equilibrium pressure is sampled before perturbation of fluid flow begins at 66, and in the preferred context of the invention, this may also represent a sampling of fluid pressure after perturbation of fluid flow has been completed, before proceeding with calculation of resistance and compliance. A series of pressure samplings are taken and added for a given period of time, at 68, and when the period of time for sampling at 70 is completed, the mean equilibrium pressure for the system is determined at 72. As is shown at 74, an infusion pump is switched in to begin running and to continue running until a predetermined volume (Q) of fluid has been delivered. While the pump is running at 74, the pressure signal produced by the pressure transducer will be sampled, and the sum of the difference between the pressure and the mean equilibrium pressure will be accumulated. Sampling at 76, determination of the difference between the sample pressure and the mean equilibrium pressure at 78, and the summing of this difference at 80 will continue for the determination of the integral for calculating resistance, and the accumulation of the sum of the pressure difference times the time for calculation of compliance at B2, will continue until equilibrium is attained at 84.

It should be noted that the first "DONE" block at 70, which controls calculation of mean equilibrium pressure is controlled by specifying the time over which the sum is to be performed. This period of time may be determined during set up of the instrument, and may vary with the flow rate. The second "DONE" block at 84, which controls the accumulation of the integrals for determining resistance and compliance, is also controlled by specifying the time over which the summing operations are to be performed. This period of time is initially determined during set up, but may be adjusted adaptively, based upon the time the pressure actually requires to return to equilibrium. Resistance is thereafter determined at 86 and compliance is determined at 88, as described above. The value "$T_0$" which appears in the last block 88 in the flow chart represents the value of the integral $$T_0 = \frac{\int_0^\infty t(F(t) - F_{eq}) dt}{\int_0^\infty (F(t) - F_{eq}) dt} \qquad (12)$$

which appears in Equations 10 and 11 above. This value may be derived from the known design characteristics of the particular pump, and the length of time of flow perturbation.

Figure 4:
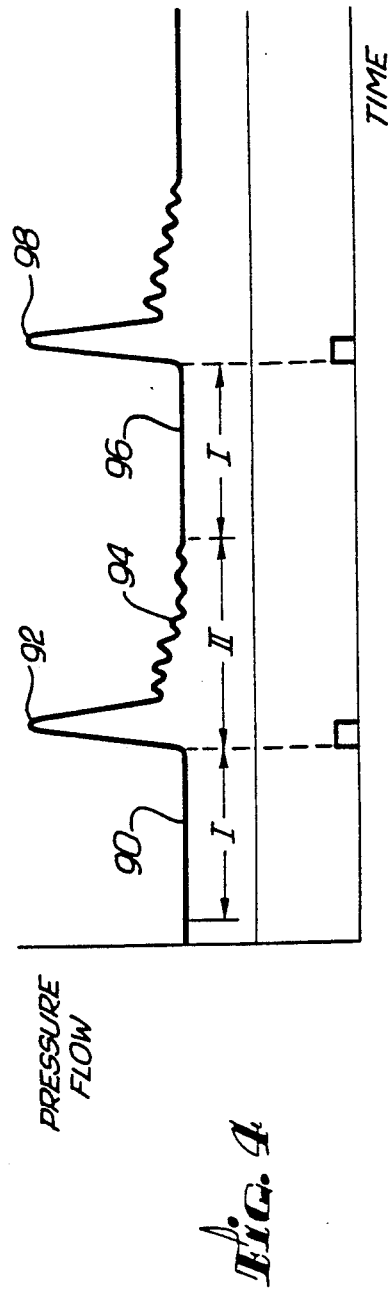
FIG. 4 is a graphical representation of pressure response and equilibrium pressure sensed by the system.

Referring to FIG. 4, showing a typical pressure wave form, the region 90 indicated by (I) is used to obtain an average value of equilibrium pressure, $P_{eq}$. The region 92 represents a first pressure peak in response to the beginning of perturbation of flow in the system. The region 94 represents the time period (II) used for integration of the pressure response due to the volume of flow, or bolus, produced by the infusion pump. The pressure response to perturbation of the fluid flow is completed, whereupon there is a second region 96 representing a time for again sampling equilibrium pressure, and the perturbation of flow begins again at the second pressure peak 98.

In the foregoing description, it has been demonstrated that the system and method of the invention for detecting abnormalities in infusion of parenteral fluid from a parenteral fluid delivery system to a patient provides determinations of fluid flow parameters of resistance and compliance, which may be observed by an operator, and an alarm responsive to these parameters, to signal potentially dangerous situations.

Important advantages of the invention are that the absolute value of resistance to fluid flow, and the absolute value of the compliance of the vascular tissue into which fluid is being infused, are directly and objectively related to the nature and quality of fluid infusion at the infusion site. It is also significant that as they are determined according to the present invention, these parameters are immune to changes in background pressure due to patient motion, respiration, and the like. The parameters are also immune to changes in flow rate, since the current flow rate is automatically taken into account in making the measurements. The method and system of the invention also have the significant advantage of being insensitive to vibration of the infusion set tubing, because of filtering which is inherent in an integral method, when typical vibrations have periods which are shorter than the length of the integral. The advantage is dramatic in comparison to derivative methods, which are based upon derivatives of pressure, which are inherently noise enhancing. The invention further provides for effective measurement of resistance and compliance at low flow rates. The invention is nevertheless not restricted to being effective only at low flow rates.

Although one specific embodiment of the invention has been described and illustrated, it is clear that the invention is susceptible to numerous modifications and embodiments within the ability of those skilled in the art and without the exercise of the inventive faculty. Thus, it should be understood that various changes in form, detail and application of the present invention may be made without departing from the spirit and scope of this invention.

I claim:

1. A system for detecting abnormalities in infusion of parenteral fluid from a parenteral fluid delivery system to a patient comprising:
   a) infusion means for producing a perturbation of said fluid flow by varying the rate of fluid flow from an equilibrium flow rate with a specific volume of fluid;
   b) sensor means for measuring pressure of said fluid over a period of time and adapted to generate a signal representing a pressure response of said fluid to said perturbation and a signal representing an equilibrium pressure level;
   c) first integrator means operatively connected to said sensor means for determining a first integral of the difference between said equilibrium pressure signal and said pressure response signal over time, and for generating a signal representing said first integral;
   d) means for determining resistance to said infusion of fluid from the delivery system adapted to scale said first integral signal according to said specific volume, and for producing a signal representing the resistance to fluid flow;
   e) second integrator means for determining a second integral by multiplying the difference between said pressure response signal over time and said equilibrium pressure signal by a value representing said time, and integrating the resultant product with respect to said time, and adapted to generate a signal representing said second integral determined; and
   f) means responsive to said first and second integrator means for determining compliance of said fluid delivery system by dividing said second integral signal by said first integral signal to produce a signal representing an effective time constant, and by scaling said effective time constant by said previously determined resistance to produce a signal representing compliance of said fluid delivery system.

2. The system of claim 1, further including memory means for receiving and storing reference values corresponding to said resistance, compliance and time constant signals;
- comparator means for comparing at least one of said signals with at least one corresponding reference value to determine a difference therebetween; and
- output means operatively connected to said comparator means for providing an indication of the value of at least one said difference.

3. The system of claim 2, wherein said output means comprises alarm means.

4. The system of claim 1, further including means for displaying values representative of at least one of said resistance, said compliance, said equilibrium pressure, and said effective time constant.

5. The system of claim 1, wherein said means for measuring pressure includes means for determining said equilibrium pressure from at least one measurement of pressure at a time when said fluid is not perturbed.

6. The system of claim 1, wherein said first integrator means is adapted to determine said first integral during a period of time in which said pressure response of said fluid is being measured.

7. The system of claim 1, wherein said second integrator means is adapted to determine said second integral during a period of time in which said pressure response of said fluid is being measured.

8. The system of claim 1, wherein said infusion means is adapted to produce a series of pulses of said fluid with periods of zero flow intervening between said pulses.

9. The system of claim 1, wherein said infusion means is adapted to increase said fluid flow to a rate above an original rate of flow at said equilibrium pressure for a predetermined period of time and return said rate of flow to said original rate of flow.

10. The system of claim 1, wherein said infusion means is adapted to decrease said fluid flow to a rate below an original rate of flow at said equilibrium pressure for a predetermined period of time and return said rate of flow to said original rate of flow.

11. The system of claim 1, wherein said infusion means is adapted to increase said fluid flow rate above an original rate of flow at said equilibrium pressure, allow said fluid flow rate to return to a said original rate of flow, decrease said fluid flow rate below said original rate of flow, and return said rate of flow to said original rate of flow.

12. The system of claim 1, wherein said infusion means is adapted to produce a cyclic perturbation of said fluid flow, and to vary the character of cycles in said cyclic perturbation in a predetermined manner.

13. The system of claim 7, further including means connected to said second integrator means for generating a signal representing an effective constant time by dividing said second integral signal by said period of time in which said pressure response is measured.

14. The system of claim 1, including means adapted to receive said resistance signal, said compliance signal, said equilibrium pressure signal, and said effective time constant signal, for comparing said signals taken together with a pattern of corresponding reference signals, and for determining a total pattern of deviation of said signals from said pattern of reference signals, and for generating an alarm when said deviation pattern is outside a predetermined range of values.

15. The system of claim 1, wherein said first and second integrator means are microprocessor means.

16. The system of claim 1, wherein said first and second integrator means are electrical analog means.

17. The system of claim 1, wherein said infusion means includes positive displacement pump.

18. The system of claim 1, wherein said infusion means includes a peristaltic pump.

19. The system of claim 1, wherein said infusion means includes a variable duty cycle controller.

20. The system of claim 1 wherein the compliance determining means subtracts a flow factor which is proportional to the time of flow perturbation of the specific volume of fluid from the quotient of the second integral divided by the first integral prior to sealing the quotient by the resistance.

21. The system of claim 20 wherein the compliance determining means determines the flow factor by dividing an integral of the difference between the equilibrium flow and the flow perturbation over time into an integral of the time multiplied by the difference between the equilibrium flow and the flow perturbation over time.

22. The system of claim 1 wherein said first and second integrals are determined over a time period extending until the fluid flow returns to equilibrium.

23. The method of detecting abnormalities in infusion of parenteral fluid from a parenteral fluid delivery system to a patient, the delivery system having an equilibrium flow rate, comprising the steps of:
a) producing a perturbation of said fluid flow by varying the rate of fluid flow from an equilibrium flow rate with a specific volume of fluid;
b) measuring the pressure of said fluid over a period of time, generating a signal representing an equilibrium pressure level, and generating a signal representing a pressure response of said fluid to said perturbation;
c) determining a first integral of the difference between said equilibrium pressure signal and said pressure response signal over time, and generating a signal representing said first integral;
d) determining resistance to fluid flow in the delivery system by scaling said first integral according to said specific volume, and generating a signal representing resistance to fluid flow;
e) determining a second integral by multiplying the difference between said pressure response signal over time and said equilibrium pressure signal by a value representing said time, and integrating the resultant product with respect to said time, and generating a signal representing said second integral; and
f) determining compliance of the fluid delivery system by dividing said second integral signal by said first integral signal to produce a signal representing an effective time constant of said fluid delivery system and scaling said time constant signal by said previously determined resistance to produce a signal representing compliance of said fluid delivery system.

24. The method of claim 23, further including the steps of comparing at least one of said signals with at least one corresponding reference value to determine a difference between said signal and said reference value; and generating an alarm signal when said difference is greater than a predetermined alarm value.

25. The method of claim 23, further including the step of displaying values representing at least one of said resistance, said compliance, said equilibrium pressure, and said effective time constant.

26. The method of claim 23, wherein the step of measuring pressure includes determining said equilibrium pressure from at least one measurement of pressure at a time when said fluid is not perturbed.

27. The method of claim 23, wherein said first integral is determined during a period of time in which said pressure response of said fluid is being measured.

28. The method of claim 23, wherein said second integral is determined during a period of time in which said pressure response of said fluid is being measured.

29. The method of claim 23, wherein said perturbation of said fluid flow is produced by a series of pulses of said fluid with periods of zero flow intervening between said pulses.

30. The method of claim 23, wherein perturbation of said fluid flow is produced by increasing said fluid flow to a rate above an original rate of flow at said equilibrium pressure for a predetermined period of time, and returning said rate of flow to said original rate of flow.

31. The method of claim 23, wherein said perturbation of fluid flow is produced by decreasing said fluid flow to a rate below an original rate of flow at said equilibrium pressure for a predetermined period of time, and returning said rate of flow to said original rate of flow.

32. The method of claim 23, wherein said perturbation of fluid flow is produced by increasing said fluid flow rate above an original rate of flow at said equilibrium pressure for a predetermined period of time, allowing said fluid flow rate to return to said original flow rate, decreasing said fluid flow rate below said original rate of flow for a second predetermined of time, and returning said rate of flow to said original rate of flow.

33. The method of claim 23, wherein said perturbation of fluid flow is a cyclic perturbation, and the character of cycles in said cyclic perturbation is varied in a predetermined manner.

34. The method of claim 23, wherein said resistance signal, said effective compliance signal, said equilibrium pressure signal and said effective time constant signal are compared as a group with a pattern of corresponding reference signals, a total pattern of deviation of said signals from said pattern of said reference signals is determined, and an alarm is generated when said deviation pattern falls outside a predetermined set of value ranges.

35. The method of claim 23 wherein the step of determine compliance further includes subtracting a flow factor which is proportional to the time of flow perturbation of the specific volume of fluid from the quotient of the second integral divided by the first integral prior to scaling the quotient by the resistance.

36. The method of claim 35 wherein the step of determining compliance comprises the step of determining the flow perturbation over time into an integral of the time multiplied by the difference between the equilibrium flow and the flow perturbation over time.

37. The method of claim 23 wherein the steps of determining the first and second integrals comprise determining said integrals over a time period extending until the fluid flow returns to equilibrium.

38. A system for determining compliance in infusion of a fluid to a patient by a fluid delivery system, the fluid delivery system having an equilibrium flow rate, comprising:
   a) an infusion pump for producing a perturbation in said fluid flow by varying the rate of fluid flow from the equilibrium flow rate with a specific volume of fluid;
   b) a pressure sensor for measuring the pressure of the fluid in the fluid delivery system over a period of time and adapted to provide a perturbation pressure signal representing the pressure response of said fluid to said perturbation and an equilibrium pressure signal representing an equilibrium fluid pressure;
   c) a resistance calculator for determining the resistance to the infusion of fluid and providing a resistance signal representative thereof;
   d) a first integrator which receives the perturbation pressure signal and the equilibrium pressure signal and determines a first integral of the difference between said equilibrium pressure signal and said perturbation pressure signal over time, and for providing a pressure difference signal representative thereof; and
   e) a compliance calculator which receives the perturbation pressure signal and the equilibrium pressure signal and determines a second integral by multiplying the difference between the perturbation pressure signal and said equilibrium pressure signal over time by a value representing said time, and integrating the resultant product with respect to said time, and adapted to provide a compliance signal representing said second integral divided by said first integral, the quotient of which is divided by the resistance signal.

39. The system of claim 38 in which the resistance signal is provided by dividing the pressure difference signal by the specific volume of fluid.

40. The system of claim 38 wherein said first and second integrals are determined over a time period extending until the fluid flow returns to equilibrium.

41. The system of claim 38 further comprising an alarm comparator which receives the compliance signal and compares it to a predetermined threshold value and provides an alarm signal based on the comparison.

42. The system of claim 38 wherein the compliance calculator subtracts a flow factor which is proportional to the time of flow perturbation of the specific volume of fluid from the quotient of the second integral divided by the first integral prior to scaling the quotient by the resistance.

43. The system of claim 42 wherein the compliance calculator determines the flow factor by dividing an integral of the difference between the equilibrium flow and the flow perturbation over time into an integral of the time multiplied by the difference between the equilibrium flow and the flow perturbation over time.

44. A system for detecting abnormalities in infusion of fluid to a patient from a fluid delivery system, the fluid delivery system having an equilibrium flow rate, comprising:
   a) an infusion pump for producing a perturbation in said fluid flow by varying the rate of fluid flow from the equilibrium flow rate with a specific volume of fluid;
   b) a pressure sensor for measuring the pressure of the fluid in the fluid delivery system over a period of time and adapted to provide a perturbation pressure signal representing the pressure response of said fluid to said perturbation and an equilibrium pressure signal representing an equilibrium fluid pressure;

c) a resistance calculator for determining the resistance to the infusion of fluid and providing a resistance signal representative thereof;

d) a first integrator which receives the perturbation pressure signal and the equilibrium pressure signal and determines a first integral of the difference between said equilibrium pressure signal and said perturbation pressure signal over time, and for providing a pressure difference signal representative thereof;

e) a compliance calculator which receives the perturbation pressure signal and the equilibrium pressure signal and determines a second integral by multiplying the difference between the perturbation pressure signal and said equilibrium pressure signal over time by a value representing said time, and integrating the resultant product with respect to said time, and adapted to provide a compliance signal representing said second integral divided by said first integral, from the quotient of which is subtracted a flow factor which is proportional to the time of flow perturbation of the specific volume of fluid, all of which is divided by the resistance signal; and f) an alarm comparator which receives the resistance signal and compares it to a threshold value and provides an alarm based on the comparison and receives the compliance signal and compares it to a threshold value and provides an alarm signal based on the comparison.

45. The system of claim 44 in which the resistance signal is provided by dividing the pressure difference signal by the specific volume of fluid.

46. The system of claim 45 wherein the first and second integrals are determined over a time period extending until the fluid flow returns to equilibrium.

47. The system of claim 44 wherein the first and second integrals are determined over a time period extending until the fluid flow returns to equilibrium.

* * * * *

UNITED STATES PATENT AND TRADEMARK OFFICE
CERTIFICATE OF CORRECTION

PATENT NO. : 5,087,245
DATED : February 11, 1992
INVENTOR(S) : David Doan It is certified that error appears in the above-identified patent and that said Letters Patent is hereby corrected as shown below:

Column 2, line 46, delete "into"

Column 3, line 39, (Equation 7) change "dt" to --dt'--

IN THE DETAILED DESCRIPTION OF THE INVENTION:

Column 9, line 13, change "B2" to --82--

Column 13, line 56, change "the flow perturbation" to
 --the flow factor by dividing an integral of the difference between the equilibrium flow and the flow perturbation--

Signed and Sealed this

Fourth Day of May, 1993

Attest:

MICHAEL K. KIRK

Attesting Officer

Acting Commissioner of Patents and Trademarks